United States Patent [19]
Taylor

[11] Patent Number: 4,998,620
[45] Date of Patent: Mar. 12, 1991

[54] STERILIZED PACK OF FABRIC ARTICLES

[75] Inventor: Jeffrey L. Taylor, Cincinnati, Ohio

[73] Assignee: Standard Textile Company, Inc., Cincinnati, Ohio

[21] Appl. No.: 360,361

[22] Filed: Jun. 2, 1989

Related U.S. Application Data

[62] Division of Ser. No. 149,363, Jan. 28, 1988, abandoned.

[51] Int. Cl.⁵ .................... B65D 85/16; A61B 19/00
[52] U.S. Cl. .................... 206/440; 206/442; 206/451; 206/494; 206/812
[58] Field of Search .................... 206/438–440, 206/494, 812, 451, 83.5, 442; 229/87 R; 53/399; 100/33 P B

[56] References Cited

U.S. PATENT DOCUMENTS

| | | | |
|---|---|---|---|
| 829,923 | 8/1906 | Lee | 206/440 |
| 1,909,407 | 5/1933 | Hudson | 206/494 |
| 2,222,072 | 11/1940 | Harvey | 206/494 X |
| 3,061,087 | 10/1962 | Scrivens et al. | 206/439 |
| 3,442,732 | 5/1969 | Stensaker et al. | 100/33 PB |
| 3,442,735 | 5/1969 | Stensaker | 53/399 X |
| 3,749,622 | 7/1973 | Sato et al. | 53/399 X |
| 3,991,881 | 11/1976 | Augurt | 206/439 |
| 3,997,901 | 10/1976 | Dullinger | 206/451 |
| 4,121,714 | 10/1978 | Daly et al. | 206/439 X |
| 4,483,438 | 11/1989 | Kobiella | 206/83.5 |
| 4,540,614 | 9/1985 | Omori | 206/451 |

Primary Examiner—Bryon P. Gehman
Attorney, Agent, or Firm—Kinney & Schenk

[57] ABSTRACT

A pack of laundered, folded and sterilized articles and method of packaging same are provided wherein such articles have at least one band disposed in encircling relation around the pack and holding same in a compact manner wherein the band has overlapping fused end portions and such band is made of a material which does not contaminate the pack.

5 Claims, 2 Drawing Sheets

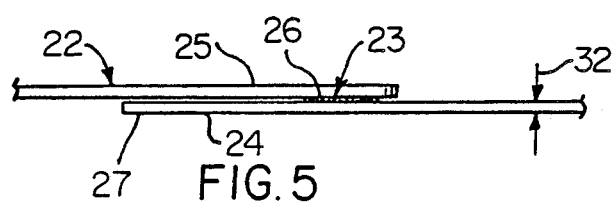
FIG. 5
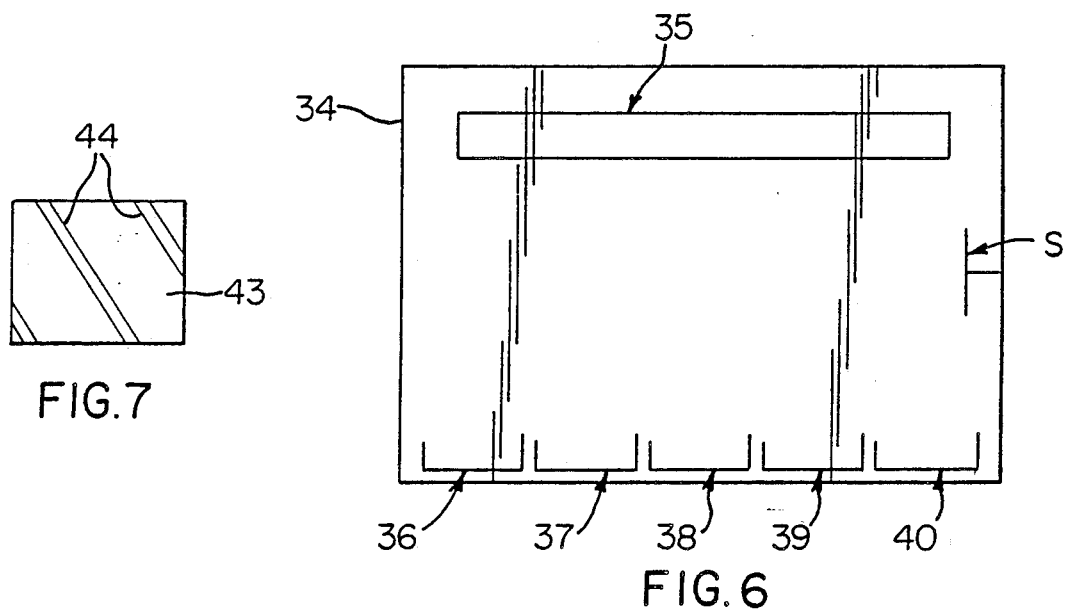
FIG. 7
FIG. 6
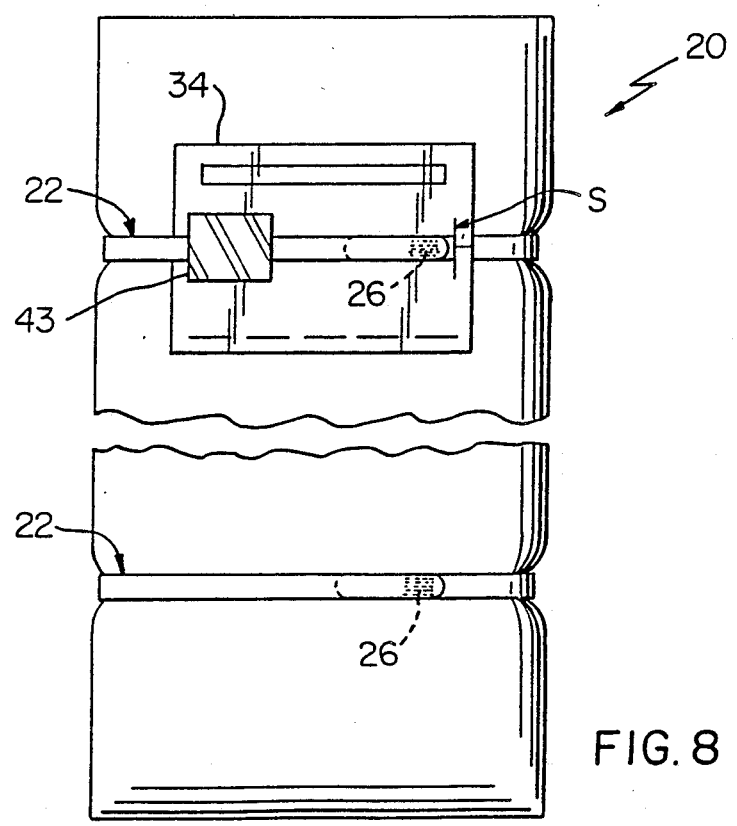
FIG. 8

STERILIZED PACK OF FABRIC ARTICLES

This is a division of application Ser. No. 149,363 filed Jan. 28, 1988, now abandoned.

BACKGROUND OF THE INVENTION

1. Field of the Invention

This invention relates to a pack of laundered, folded, and sterilized articles, and more particularly to articles adapted for surgical use in a hospital environment and to a method of packaging such articles.

2. Prior Art Statement

It is known in the art to provide a pack of laundered, folded and sterilized articles made of fabric material and which have band means disposed in encircling relation around the pack and holding same in a compact manner. In certain previous instances, such a known pack has been held together with a simple string. In other previous instances, such a pack has been held together by a tape which has an adhesive material which contacts the outer article of the pack. However, it has been found that during reprocessing of the pack, if the tape material is not properly removed from the fabric, the adhesive material provided on such a tape gets into the interstices of the fabric material of the outer article of the pack and the residual causes stains and potential harbors where bacteria can collect and grow. Especially in applications where such articles are used during surgery, it is very important that the articles be free of bacteria. In tape-held packs of the character mentioned the adhesive material from the tape is generally visible on the articles upon inspection of such articles prior to use, and once discovered the articles are reprocessed thereby resulting in multiple washings with their added costs; and, even with multiple washings there is no assurance that the adhesive will ever be removed whereby the same procedure might be repeated, further increasing costs.

The previous packs of laundered, folded, and sterilized articles, including those in the form of articles used in surgery, have deficiencies in that they have either been held together by simple strings which do not provide an adequate and secure closure and will produce airborne contaminates when cut or broken, or have been held together by adhesive tape in which the adhesive can migrate to each article engaged by the tape and provide harbors for bacteria and added costs to process each article on which adhesive is discovered.

SUMMARY OF THE INVENTION

Accordingly, it is a feature of this invention to provide a pack of the character mentioned which overcomes the above-mentioned deficiencies.

Another feature of this invention is to provide a new pack of laundered, folded, and sterilized articles which has band means disposed in encircling relation around the pack and holding same in a compact manner.

In accordance with one embodiment of this invention, the band means has overlapping fused end portions and the band means is made of a material which does not contaminate the pack.

Another feature of this invention is to provide a new method of packaging, sterilizing, and identifying a plurality of fabric articles after washing and drying thereof which comprises the steps of folding the articles to define a pack thereof, disposing band means around the pack to hold same in a compact manner, and sterilizing the pack by subjecting same to a sterilization environment.

In accordance with one embodiment of the method of this invention a preparation step is utilized which comprises providing a strip of thermoplastic material to be used to define the band means with the thermoplastic material being a material which does not contaminate the pack, and the disposing step comprises disposing opposite end portions of the strip in overlapping relation and then fusing the opposite end portions to define the band means.

Accordingly, it is an object of this invention to provide a new pack of laundered, folded, and sterilized articles wherein such pack has one or more of the novel features of this invention as set forth above or hereinafter shown o described.

Another object of this invention is to provide a new method of packaging, sterilizing, and identifying a plurality of fabric articles after washing and drying thereof wherein such method has one or more of the novel features of this invention as set forth above or hereinafter shown or described.

Other features, objects, uses, and advantages of this invention are apparent from a reading of the following description which proceeds with reference to the accompanying drawings forming a part thereof.

BRIEF DESCRIPTION OF THE DRAWINGS

The accompanying drawings show present preferred embodiments of this invention, in which

FIG. 5 is a side view illustrating the overlapped fused end portions of the strip of FIG. 1;

FIG. 6 is an enlarged view illustrating a card comprising the pack of FIG. 1 and such card is shown with a T-shaped slit therein which is used in the FIG. 8 embodiment;

FIG. 7 is a view illustrating a tape which comprises the pack of FIG. 1 and is used to hold the card to the band of such pack;

FIG. 8 is a view illustrating another exemplary embodiment of a pack of this invention which utilizes a plurality of band means.

DESCRIPTION OF THE PREFERRED EMBODIMENTS

Figure 1:
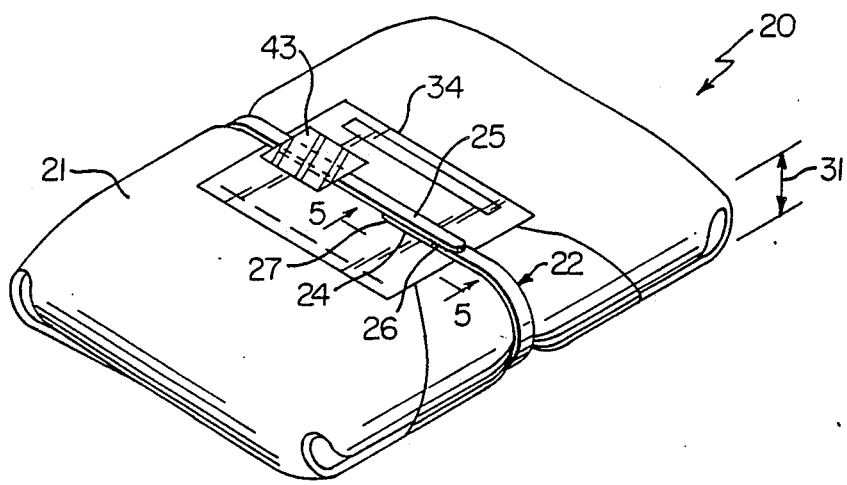
FIG. 1 is an isometric view of one exemplary embodiment of a pack of this invention.

While the various features of this invention are hereinafter illustrated and described as being particularly adapted to provide a pack of laundered, folded and sterilized articles such as fabric articles in the form of towels which are used during hospital surgical procedures, it is to be understood that the various features of the invention can be utilized singly or in various combinations thereof to provide a pack for other laundered, folded, and sterilized articles which may be used in hospital, nursing home, or the like, as desired.

Therefore, this invention is not to be limited to only the embodiments illustrated in the drawings, because the drawings are merely utilized to illustrate exemplary ones of the wide variety of uses of this invention.

Reference is now made to FIG. 1 of the drawings which illustrates one exemplary embodiment of a pack of this invention which is designated generally by the reference numeral 20. The pack 20 of this example is a pack of laundered, folded, and sterilized articles 21 which are in the form of surgical towels utilized in hospital surgical procedures. However, as indicated earlier such a pack may be a pack of similar articles of any type where it is desired to have a sterilized article.

Figure 2:
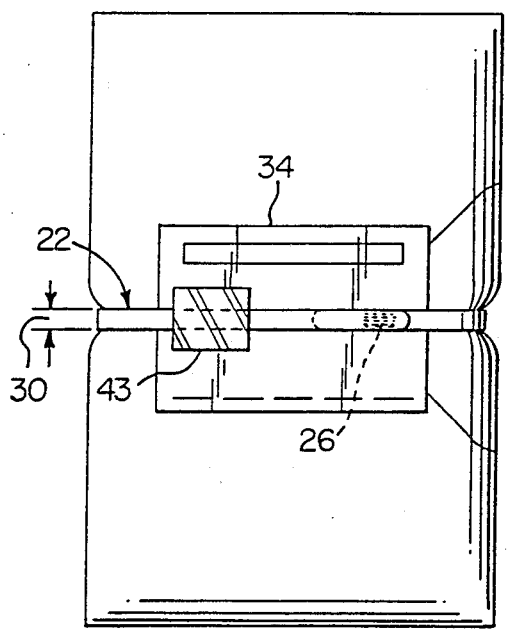
FIG. 2 is a top-plan view of the pack of FIG. 1.

The pack of articles 21 has band means which in this example is made of a flat strip of thermoplastic material and such band means and strip are designated by the reference numeral 22. The band means 22 is disposed in encircling relation around the pack and holds same in a compact manner and, as illustrated in FIGS. 1, 2 and 5. The band means has overlapping fused end portions as shown particularly at 23 in FIG. 5.

In accordance with the teachings of this invention, the band means is made of a material which does not contaminate the pack of articles; and, in particular, inasmuch as the band means or strip 22 does not have adhesive material or other material likely to be transferred or migrate from such band means or strip to the pack, the articles 21 in the pack 20 remain unsoiled or uncontaminated by such band means 22.

Referring now to FIG. 5 of the drawings, it will be seen that the overlapping fused end portions illustrated at 23 comprise an inner end portion 24 and an outer end portion 25 which are fused together at a particular location which in this example is designated by the reference numeral 26 of the overall band means 22. The inner end portion 24 has a terminal end 27 which extends beyond the location 26 and the terminal end 27 is adapted to be rotated roughly 180 degrees to expose same so that it can be grasped manually, or by other means, as indicated by the arrow at 28 in FIG. 3 to separate the end portions 24 and 25 at location 26 and thereby remove the band means from encircling relation as shown at 29 in FIG. 4.

Referring now again to FIG. 2 of the drawings, it is seen that the flat strip 22 which defines the band means has a width dimension 30 which is a small fractional part of any dimension of the pack including the thickness 31 (FIG. 1) of such pack. Further, it will be seen that the flat strip 22 has a thickness 32, seen in FIG. 5, which is a small fractional part of the width dimension 30.

The pack 20 also has a card 34 disposed between the pack and the strip or band means 22 and the card is made of a material that does not contaminate the pack. The card is shown on the pack in FIGS. 1 through 4 and 8 and is illustrated in more detail in FIG. 6. The card 34 serves to provide date identifying the contents of the pack and providing data relating to sterilization and shelf life of such pack. In particular, the contents of the pack are usually provided at a location indicated at 35 on such card and the card is a card which is adapted to be marked to provide the necessary data mentioned previously and in the for of data identifying the contents of the pack and data relating to the sterilization and shelf life of the pack. The card 34 may be made of any suitable material (and may be)preprinted with pack-content information or is adapted to be marked manually with an ordinary writing instrument such as a pencil, ballpoint pen, or the like, with the same information.

As previously mentioned, the pack 20 is a sterile pack and the card 34 also has several locations thereon where certain data is provided dealing with sterilization of the pack. In particular, such card has a location at 36 where the expiration date of the pack itself is marked which, in essence, is the shelf life after which the pack 20 is no longer considered sterile. In addition, at location 37 the date is written on the card when the sterilization was achieved, at location 38 the machine or sterilizer in which sterilization was achieved is written, at location 39 the load number or autoclave load is written; and finally, at location 40 the party monitoring the sterilization initials the information card 34. It will be appreciated that the load number written at 39 is used primarily in the event of recalls and a particular batch needs to be returned for any reason such as contamination, or the like.

The pack 20 also utilizes a small strip of adhesive tape means 43 and such tape means engages an outside surface of only the card 34 and the flat strip 22. The tape means or tape 43 has integral indicator means or strips 44 which indicate whether the tape 22 and its pack 20 have been subjected to a sterilization environment. In particular, the tape 43 is illustrated in more detail in FIG. 7 of the drawings and it will be seen that such tape has indicator bands or strips 44 which are made of a material which may be an ink means 44 or material which changes color on being subjected to a sterilization environment. In the case of a tape 43 utilized on the pack 20 which is sterilized by a steam process or an autoclave process, the strips 44 of the tape 43 change from white to black once the tape 43 is subjected to the autoclave process. Of course, the pack 20 with the band means 22 therearound and the tape 43 holding the card 34 in position are all subjected to the heated environment produced by the autoclave.

The band means or flat strip of thermoplastic tape 22 may be made of any suitable material known in the art. However, it is preferably made of a polymeric material such as polyester, nylon, or polypropylene. In addition, the thermoplastic material is preferably the type of material that is substantially non heat shrinkable when subjected to a sterilization environment such as the environment that would be produced by a steam autoclave or the like. It will also be appreciated that in using polyester, nylon , or polypropylene such a material has optimum structural integrity, is free of adhesive means, or the like, and even when subjected to an autoclave environment or steam environment retains its structural integrity and does not break down or tend to be transferred to the pack around which it is disposed whereby such material provides optimum results in an application such as this.

In the pack 20, it will be seen that such pack utilizes band means or a single band means or strip 22. However, it will be appreciated that a particular pack may be of sufficient size that it requires a plurality of band means or thermoplastic strips. In particular, and as illustrated in FIG. 8 of the drawings, it will be seen that a modification of a pack is illustrated and such pack is also designated by the reference numeral 20. The pack 20 of FIG. 8 is of sufficient size that it has a plurality of two band means or thermoplastic strips 22 and in the pack 20 of FIG. 8 also has a card 34 and an adhesive tape 43 holding the card in position against one of the band means or tapes 22. The card 34 may also be fastened to the pack and band means 22 using a T-shaped or key-hole-shaped slit S which may be provided therein, if desired, and as shown in FIGS. 6 and 8, for example. However, it will be appreciated that when a T-shaped or key-hole slit S is used to fasten the card beneath the band, the card preferably has its top surface printed with some of the same type of ink means 44 that is used on the autoclave tape 43 because the tape will not be necessary when a slit is used. Therefore, the card with the ink means 44 on it acts as the indicator that the pack has been exposed to a sterilization environment.

In a similar manner as described previously in connection with the pack 20 and the band means 22 thereof, each of the band means 22 of the pack 20 of FIG. 8 has overlapping fused end portions at location 23 and each of the band means is made of a material which does not contaminate the pack; and, as before, such band means may be of a thermoplastic material such as polyester, nylon, or polypropylene.

The band means 22 whether in the form of a single band means as illustrated in the pack 20 of FIG. 1 or a plurality of band means 22 as illustrated in the pack 20 of FIG. 8 is applied utilizing a machine which is employed for this purpose, and such a machine is often referred to as a strapping machine. It will be appreciated that such machine (not shown) is of a type well known in the art and serves to fuse overlapping end portions of the band means as is known in the art so as to provide band means or a band which completely encircles its pack 20 and serves to hold the pack in a compact manner.

Having described the pack 20 of this invention in detail, it will be appreciated that in accordance with this invention a method of packing, sterilizing, and identifying a plurality of articles such as fabric articles after washing and drying thereof is provided. It will be appreciated that in practicing the method of this invention, the articles are folded to define a pack thereof and the folding is, of course, achieved after drying; and, in the case of fabric articles used in a hospital and in the form of surgical towels or the like, the folding is achieved after the ironing or tumble drying and an ironing or folding machine may be used in the folding process.

After folding the articles to define the pack thereof, one or more band means or bands is disposed around the pack to hold same in a compact manner. The pack is then sterilized by subjecting same to a sterilization environment and the sterilization environment may be in the form of a steam autoclave or similar environment. It will be appreciated that in accordance with the teachings of this invention a strip of thermoplastic material is provided and used to define the band means and the thermoplastic material is a material which preferably does not shrink upon being subjected to a sterilization environment and certainly such material is a material that does not contaminate the pack. In disposing of the band means around a pack to be sterilized, it will be appreciated that opposite end portions of the strip are disposed in overlapping relation and the opposite end portions are fused as is known in the art to define a particular band means encircling a back so as to hold same in a compact manner. As previously described in the description of the pack 20 and the constituents thereof, the end portions of the strip used to define the band means comprise an inner end portion and an outer end portion and the fusing step comprises fusing the end portions at a particular location along the strip so that the inner end portion has a terminal end which extends beyond the location specified.

Figure 3:
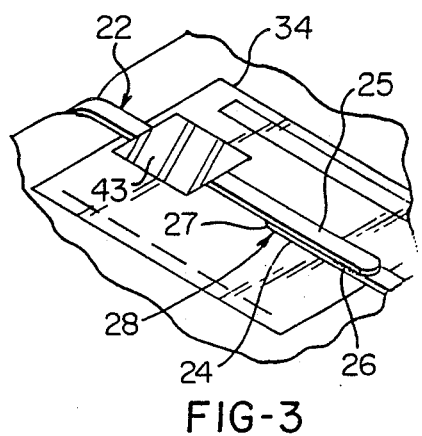
FIG. 3 is an enlarged fragmentary isometric view showing overlapped fused end portions of a flat strip of material comprising band means encircling the pack.
Figure 4:
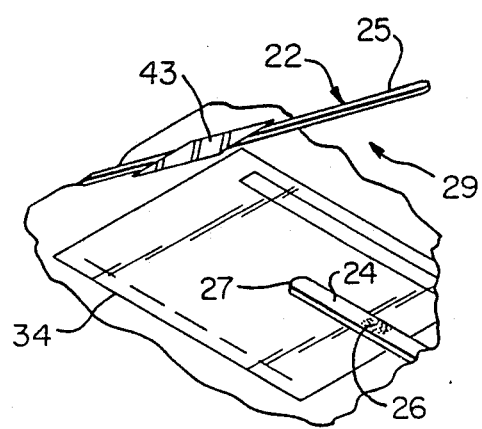
FIG. 4 is a view similar to FIG. 3 illustrating the end portions pulled apart.

The terminal end of the inner end portion is adapted to be grasped manually to separate the end portions at location 26 by first rotating the band means manually roughly 180 degrees and thereby remove the band means from its encircling relation as previously described and shown in connection with FIGS. 3 and 4 of the drawings. FIG. 4 illustrates end 27 after it has been pulled apart from the outer end portion.

In this disclosure of the invention, the pack 20 has been described as being a pack of fabric articles, such as surgical towels which have been sterilized for hospital use. However, it will be appreciated that the concepts of this invention may be utilized to provide packs of other articles in which sterilization is required, and in which it is desired to provide band means in encircling relation around such articles without contaminating the articles themselves with the encircling band means.

Thus, it is seen from the above description that this invention provides a new pack of laundered, folded, and sterilized articles.

In addition, it is seen from the above description that this invention provides a new method of packaging, sterilizing, and identifying a plurality of fabric articles.

It has been disclosed in the above presentation that the contents of the card 34 are usually provided at a location indicated at 35 on such card and location 35 is shown at the top portion of the card, as viewed in FIG. 6. However, it will be appreciated that location 35 may be any other desired location on card 34 such as at the bottom portion of card 34, for example.

In this disclosure, terms such as top, inner, outer, bottom, etc., have been used throughout; however, it is to be understood that these terms have been utilized for ease of description and should not be considered limiting in any way.

While the forms and methods of this invention now preferred have been illustrated and described as required by the Patent Statute, it is to be understood that other forms and method steps can be utilized and still fall within the scope of the appended claims wherein each claim sets forth therein what is believed to be known in the art prior to this invention in that portion of each claim that is presented before the term "the improvement" and sets forth what is believed to be new in the art according to this invention in that portion of each claim that is presented after the term "the improvement" wherein it is believed that each claim sets forth a novel, useful, and unobvious invention within the purview of the Patent Statute.

What is claimed is:

1. In a pack of laundered, folded, and sterilized articles which have band means disposed in encircling relation around said pack and holding same in a compact manner, the improvement wherein said band means has overlapping fused end portions and said band means is made of a material which does not contaminate said pack, said band means being made of a flat strip of thermoplastic material, said overlapping fused end portions comprising an inner end portion and an outer end portion which are fused at a particular location of said band means, said fused end portions at said particular location having a given fused length, said inner end portion has a terminal end which extends beyond said location, said terminal end has a graspable length, said terminal end with its graspable length being adapted to be first rotated approximately 180 degrees to expose same so that it can be grasped manually to separate said end portions at said location and thereby remove said band means from said encircling relation, and further comprising a card disposed between said pack and said flat strip, said card being made of a material that does not contaminate said pack, said card serving to provide data identifying the contents of said pack and providing data relating to sterilization and shelf life of said pack, and adhesive tape means engaging only an outside surface of only said card and said flat strip, said adhesive tape means holding said card in position against said flat strip, said adhesive tape means also having indicator means which indicate whether said tape means and its pack have been subjected to a sterilization environment.

2. A pack as set forth in claim 1 which said card comprises a card which is adapted to be marked to provide said data.

3. A pack as set forth in claim 2 in which indicator means comprises means which change color upon being subjected to a sterilization environment.

4. A pack as set forth in claim 3, in which said card is made of paper and is adapted to be marked manually with an ordinary writing instrument or mechanically stamped.

5. A pack as set forth in claim 1 in which said termoplastic material is substantially non heat shrinkable when subjected to a sterilization environment.

* * * * *